United States Patent [19]

Evrard

[11] 4,057,639

[45] Nov. 8, 1977

[54] METHOD FOR USING 3-TRICHLOROMETHYL-5-LOWER ALKOXY-1,2,4-THIADIAZOLE COMPOUNDS AS INSECTICIDES AND ACARICIDES

[75] Inventor: Thomas O. Evrard, Little Rock, Ark.

[73] Assignee: Olin Corporation, New Haven, Conn.

[21] Appl. No.: 768,238

[22] Filed: Feb. 14, 1977

[51] Int. Cl.$^2$ .......................... A01N 9/12; A01N 9/22
[52] U.S. Cl. .................................................... 424/270
[58] Field of Search ........................................ 424/270

[56] References Cited

U.S. PATENT DOCUMENTS

| | | | |
|---|---|---|---|
| 3,260,588 | 7/1966 | Schroeder | 424/270 X |
| 3,260,725 | 7/1966 | Schroeder | 424/270 X |
| 3,890,338 | 6/1975 | Wojtowicz et al. | 260/302 D |
| 3,890,339 | 6/1975 | Gavin | 260/302 D |

*Primary Examiner*—Allen J. Robinson
*Attorney, Agent, or Firm*—William A. Simons; Thomas P. O'Day; F. A. Iskander

[57] ABSTRACT

The present invention relates to a method for using selected 3-trichloromethyl-5-lower alkoxy-1,2,4-thiadiazole compounds as insecticides or acaricides.

7 Claims, No Drawings

METHOD FOR USING 3-TRICHLOROMETHYL-5-LOWER ALKOXY-1,2,4-THIADIAZOLE COMPOUNDS AS INSECTICIDES AND ACARICIDES

BACKGROUND OF THE INVENTION

I. Field of the Invention

This invention relates to a method for using selected 3-trichloromethyl-5-substituted-1,2,4-thiadiazole compounds as insecticides and acaricides.

II. Description of the Prior Art

U.S. Pat. Nos. 3,260,588 and 3,260,725 (both granted on July 12, 1966 to H. A. Schroeder) disclose using certain 3-trichloromethyl-5-substituted-1,2,4-thiadiazoles as fungicides, nematocides and herbicides. These thiadiazole compounds, in particular, 3-trichloromethyl-5-ethoxy-1,2,4-thiadiazole, have proven to be outstandingly effective soil fungicides with the 5-ethoxy-thiadiazole compound gaining wide commercial acceptance. However, while these thiadiazole compounds have been shown to be effective in controlling many species of soil fungi, it was not discovered until the present invention that certain of these compounds are equally effective against insects and acarids (i.e., mites).

SUMMARY OF THE INVENTION

The present invention, therefore, comprises a method for controlling insects or acarids by contacting them with an insecticidally or acaricidally effective amount of a 3-trichloromethyl-5-lower alkoxy-1,2,4-thiadiazole compound having the formula:

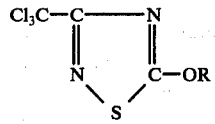

wherein R is a lower alkyl having 1 to 4 carbon atoms.

DETAILED DESCRIPTION

In accordance with the present invention, it has been found that 3-trichloromethyl-5-lower alkoxy-1,2,4-thiadiazole compounds covered by Formula (I), either singly, or in combination with each other, can be utilized as effective insecticides and acaricides. Of these compounds, 3-trichloromethyl-5-ethoxy-1,2,4-thiadiazole is preferred. This compound has already demonstrated outstanding activity as a soil fungicide and is now being produced in large commercial quantities for that purpose. This commercial fungicide product can easily be converted into insecticide or acaricide products.

In accordance with the broad concept of the invention, it is also generally contemplated that other 3-trichloromethyl-5-substituted-1,2,4-thiadiazoles, as described in the above-noted Schroeder patents, may be used in practicing the method described herein.

The 5-lower alkoxy-thiadiazole compounds used in the present invention can be prepared by any of the processes disclosed in U.S. Pat. Nos. 3,260,588; 3,260,725; 3,890,338 (granted on June 17, 1975 to J. A. Wojtowicz et al); and 3,890,339 (granted June 17, 1975 to D. F. Gavin). The entire disclosure of these patents are incorporated herein by reference. The first three of these four patents describe processes for making 3-trichloromethyl-5-ethoxy-1,2,4-thiadiazole by reacting ethanol or alkali metal ethylate with 3-trichloromethyl-5-chloro-1,2,4-thiadiazole. The last patent teaches a process for preparing 3-trichloromethyl-5-ethoxy-1,2,4-thiadiazole from trichloroacetonitrile in ethanol which serves as a solvent and reactant. The other lower alkoxy thiadiazoles used herein can be formed by comparable methods. And, of course, other conventional methods for making the compounds of Formula (I) can be utilized.

In practicing the method of the present invention, insects and acarids are contacted with an insecticidally or acaricidally effective amount of the compounds of Formula (I). It is to be understood that the term "insecticidally or acaricidally effective amount" as used in the specification and claims herein is intended to include any amount that will kill or control said insects or acarids when either employed by itself (i.e., in full concentration) or in a sufficient concentration within a carrier or other substance. Of course, this amount may be constantly changing because of the possible variations in many parameters. Some of these may include: the number and type of insects or acarids to be killed or controlled; the type of media to which the present compounds can be applied (e.g., insect breeding grounds, crops); degree of effectivenees required; and type of carrier, if any.

This step of contacting may be accomplished by applying these compounds to the insects or acarids themselves, their eggs or larvae, their habitat, breeding grounds, dietary media, such as vegetation, crops and the like, and plant and animal like, including man, which these pests may attack. Preferably, it is advantageous to apply the chemicals of the present invention to the eggs of these insects. Also preferably, these chemicals can be applied to the insect larvae, the larvae habitat or the larvae dietary media. At the egg and larvae stages of the insects' cycle, the insect is usually relatively stationary and the insecticide or acaricide normally can be applied in a more economical fashion with a greater expectation of good results.

The compounds of Formula (I) may be formulated and applied by any conventional methods that include using the chemicals alone or with a carrier or other substances which may enhance the effectiveness of the chemical or facilitate handling. Moreover, the activity of the present compounds may be broadened by the addition thereto of other known biocides.

Specific methods of formulating and applying these active compounds of Formula (I) include applying them in the form of dusts, dust or emulsion concentrates, wettable powders and concentrates, granulates, dispersions, sprays, solutions and the like. They may also be incorporated into baits upon which insects and acarids and their larvae feed.

The dusts are usually prepared by simply grinding together from about 1 to 15% by weight of the active compound of Formula (I) with a finely divided inert diluent such as walnut flour, diatomaceous earth, fullers earth, attaclay, talc or kaolin. Dust concentrates are made in similar fashion excepting that about 16 to 75% by weight of active compound is ground usually together with the diluent. In practice, dust concentrates are then generally admixed at the site of use with more inert diluent before it is applied to the plant foliage or animals which are to be protected from insect and acarid attack.

Wettable powders are generally prepared in the same manner as dust concentrates, but usually about 1 to 10% by weight of a dispersing agent, for example, an alkali metal lignosulfonate and about 1 to 10% of surfactant, such as a non-ionic surfactant, are incorporated in the formulation. For application to agronomic crops, shrubs, ornamentals and the like, the wettable powder is usually dispersed in water and applied as a spray. For treatment of warm-blooded animals, this same spray-type application may be used or the wettable powder may be dispersed in the water of a dipping trough through which the animals are driven.

Emulsifiable liquids may be prepared by dissolving the active compound in an organic solvent, such as xylene or acetone, and admixing the thus formed solution with a surfactant or an emulsifer. The emulsified liquid is then generally dispersed in water for spray or dip application.

It is also possible to formulate granulates whereby the active compounds of Formula (I) are dissolved in an organic solvent and the resulting solution is then applied to a granulated mineral or the like (e.g., bentonite, $SiO_2$ or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the active compound, or more than one active compound, of the general Formula (I) is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that the insecticide or acaricide formulations, the ingredients which may make up such formulations other than the compounds of Formula (I), and the dosages, and means of applying these formulations may include all known and conventional substances, amounts and means, respectively, that are suitable for obtaining the desired insecticidal and/or acaricidal result. And, therefore, such process parameters are not critical to the present invention.

Insecticides and acaricides of the present invention may be effective for the control of broad classes of insects and acarids and their eggs and larvae. Specific illustrations of insects wherein insecticidal activity has been shown include Southern armyworm larvae (*Spodoptera eridania*), Colorado potato beetle larvae (*Leptinotarsa decemlineata*) and *Spodoptera littoralis*.

The following examples further illustrate the present invention. All parts and percentages employed therein are by weight unless otherwise indicated.

EXAMPLE I

One microliter of 3-trichloromethyl-5-ethoxy-1,2,4-thiadiazole[1] (99% by weight pure) was applied individually to the dorsa of actively-feeding last-instar Southern armyworm larvae (*Spodoptera eridania*) and Colorado potato beetle larvae (*Leptinotarsa decemlineata*). Likewise, one microliter of a well-known insecticide, Methyl Parathion[2] (80% Technical), and one microliter of acetone were separately applied to dorsa of other larvae samples of these two insect species as controls. The results of this comparison experiment are shown in Table I below.

Table I

| Material Applied | Test Species | %Moribund[5]--Minutes After Treatment | | | | |
|---|---|---|---|---|---|---|
| | | 1 | 10 | 20 | 40 | 60 |
| Terrazole[200] | SAW[3] | 20% | 80% | 100% | — | — |
| | CPB[4] | 20 | 100 | — | — | — |
| Methyl Parathion | SAW[3] | 0 | 20 | Not Observed | 100 | — |
| | CPB[4] | 0 | 20 | | 80 | 100 |
| Acetone | SAW[3] | 0 | 0 | 0 | 0 | 0 |
| | CPB[4] | 0 | 0 | 0 | 0 | 0 |

[1]Product of Olin Corporation sold under the trademark Terrazole[200].
[2]Chemical formula: 0,0-dimethyl-o-para-phosphorthioate.
[3]Southern armyworm larvae.
[4]Colorado potato beetle larvae.
[5]Moribund is employed herein to mean loss of locomotion.

As can be seen, the thiadiazole compound of the present invention was faster acting than Methyl parathion against both species. The acetone control showed a desired inactive result. The thiadiazole compound and Methyl Parathion each induced profuse regurgitation in both Southern armyworm larvae and potato beetle larvae. The regurgitate was smeared on a filter paper substrate by both species and on the bodies of the southern armyworm larvae. There was no clear evidence of loss of body fluids throughout the integument. Both the thiadiazole compound and Methyl Parathion resulted in the collapse of the insect larvae body after cessation of movement.

EXAMPLE II

As shown in Table 2 below, various aqueous solutions were formed containing particular amounts of various insecticide concentrates (shown as parts per million (ppm) by weight of the concentrate in water). These aqueous solutions were applied to the eggs of *Spodoptera littoralis* and the percentage of unhatchable eggs with each insecticide-contained solution was determined.

Table 2

| Materials | Conc. | % Unhatchability of egg-masses at indicated conc. (PPM) | | | | | |
|---|---|---|---|---|---|---|---|
| | | 5000 | 1000 | 500 | 100 | 50 | 10 |
| Terrazole[200] | (50% EC)[1] | 95% | 90% | 60% | 50% | 40% | 20% |
| Galecron | (50% EC)[2] | 100 | 90 | 80 | 60 | 40 | 0 |
| PH 6040 (Dimilin) | (25% PW)[3] | 100 | 100 | 70 | 70 | 60 | 50 |

[1]50% by weight emulsion concentrate that also contained about 45% by weight xylene and about 5% by weight of a non-ionic surfactant.
[2]GALECRON is a well-known insecticide made by Ciba-Geigy of Switzerland. Its chemical formula is N'-(4-chloro-o-tolyl)-N,N-dimethyl-formamidine and it is known by the common name, chlorodimeform. It is also supplied in a 50% by weight emulsion concentrate.
[3]DIMILIN or PH 6040 is a well-known insecticide made by Thompson-Hayward Company. Its chemical formula is N(((4-chlorophenyl)amino) carbonyl)-2,6-difluorobenzamide and it is known by the common name, diflubenzuron. It was supplied as a finely ground 25% by weight wettable powder containing 75% by weight inert suspension diluents.

As can be seen, the thiadiazole compound of the present invention had insecticide properties that were equal or about equal to those of two well-known insecticides.

What is claimed is:

1. A method for controlling insects and acarids which comprises contacting said insects and acarids with an insecticidally or acaricidally effective amount of a 3-trichloromethyl-5-lower alkoxy-1,2,4-thiadiazole compound having the formula:

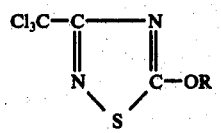

wherein R is lower alkyl having 1 to about 4 carbon atoms.

2. The method of claim 1 wherein R is ethyl.
3. The method of claim 1 wherein said compound is applied to the eggs of said insects and acarids.
4. The method of claim 1 wherein said compound is applied to the larvae of said insects and acarids.
5. The method of claim 2 wherein said compound is in an aqueous solution.
6. The method of claim 2 wherein said compound is applied to the eggs of said insects and acarids.
7. The method of claim 2 wherein said compound is applied to the larvae of said insects and acarids.

* * * * *

UNITED STATES PATENT OFFICE
CERTIFICATE OF CORRECTION

Patent No. 4,057,639   Dated November 8, 1977

Inventor(s) Thomas O. Evrard

It is certified that error appears in the above-identified patent and that said Letters Patent are hereby corrected as shown below:

Column 4, in Table I under the heading Material Applied, "Terrazole$^{200}$" should read --Terrazole®--.

Column 4, in Table I, footnote I, "Terrazole$^{200}$" should read --Terrazole®--.

Column 4, line 32, "parathion" should read --Parathion--.

Column 4, in Table II under the heading Materials, "Terrazole$^{200}$" should read --Terrazole®--.

Signed and Sealed this

Seventh Day of March 1978

[SEAL]

Attest:

RUTH C. MASON
Attesting Officer

LUTRELLE F. PARKER
Acting Commissioner of Patents and Trademarks